(12) United States Patent
Tyler

(10) Patent No.: US 7,335,222 B1
(45) Date of Patent: Feb. 26, 2008

(54) COOLING EAR MUFFS

(76) Inventor: Paul Tyler, 11401 Golf Links Rd., Oakland, CA (US) 94605

( * ) Notice: Subject to any disclaimer, the term of this patent is extended or adjusted under 35 U.S.C. 154(b) by 513 days.

(21) Appl. No.: 11/023,139

(22) Filed: Dec. 27, 2004

(51) Int. Cl.
A61F 7/00 (2006.01)
(52) U.S. Cl. .................................. 607/109; 607/108
(58) Field of Classification Search ............. 607/96, 607/108–110; 2/209
See application file for complete search history.

(56) References Cited

U.S. PATENT DOCUMENTS

| | | | | |
|---|---|---|---|---|
| 1,630,625 A | | 5/1927 | Mauriell | |
| 2,933,086 A | * | 4/1960 | Gray | 128/866 |
| 4,130,902 A | | 12/1978 | Mackenroth | 2/7 |
| 4,172,495 A | | 10/1979 | Zebuhr | 165/46 |
| 4,237,558 A | | 12/1980 | Mackenroth | 2/181 |
| 4,484,363 A | | 11/1984 | Varanese | 2/209.1 |
| 4,551,858 A | | 11/1985 | Pasternack | 2/7 |
| 4,674,134 A | * | 6/1987 | Lundin | 2/209 |
| 5,009,228 A | | 4/1991 | Clark | 128/380 |
| 5,197,292 A | | 3/1993 | McPherson | 62/56 |
| 5,327,585 A | | 7/1994 | Karlan | 2/7 |
| 5,456,703 A | * | 10/1995 | Beeuwkes, III | 607/109 |
| 5,469,579 A | | 11/1995 | Tremblay | 2/7 |
| 5,809,573 A | | 9/1998 | Bary | 2/209 |
| 5,940,880 A | | 8/1999 | Phillips | 2/7 |
| 6,093,202 A | * | 7/2000 | Dyken et al. | 607/109 |
| 6,125,474 A | | 10/2000 | Gillette | 2/171.2 |
| 6,826,287 B2 | * | 11/2004 | Myers | 381/373 |

* cited by examiner

Primary Examiner—Roy D. Gibson
(74) Attorney, Agent, or Firm—Goldstein Law Offices P.C.

(57) ABSTRACT

A pair of cooling ear muffs, for use by a user in cooling the head of the user. A pair of ear covers each have a shell and contain a reservoir for holding a chilled liquid. A sealing ring on each ear cover encircles the ear and a thermal membrane communicates heat from the ear to the reservoir. A connecting band extends between the ear covers for maintaining the ear muffs on the head of the user while holding the ear covers in position on the ears.

7 Claims, 3 Drawing Sheets

COOLING EAR MUFFS

BACKGROUND OF THE INVENTION

The invention relates to a cooled ear muff. More particularly, the invention relates to a pair of ear muffs having cooling liquid therein for cooling the head.

In cold weather, a disproportionately large amount of heat is lost through the head, in part because of the volume of blood circulating through the head and its proximity to the surface. Conversely, in hot weather, the head can quickly become overheated. In addition, the key to cooling the body lies in part with cooling the head.

In this regard, when working in hot environments, workers can be quickly overcome by the heat. Keeping the head cool, however, allow workers to endure extremely hot conditions for longer periods of time.

Several devices have been proposed to cool the head by means of a hat containing cooling apparatus. For example, U.S. Pat. Nos. 1,630,625 to Mauriell; 4,172,495 to Zebuhr; 4,484,363 to Varanese; 4,551,858 to Pasternack; 5,327,585 to Karlan; 5,469,579 to Tremblay; 5,197,292 to McPherson; 6,125,474 to Gillette; 5,940,880 to Phillips; and 4,130,902 and 4,237,558 to Mackenroth all disclose various devices for cooling the head.

A great deal of the heat circulation for the head, however, occurs within the ears. Natural heat exchangers of sorts, the ears both lose substantial heat in cold weather and generate substantial heat in hot weather. Thus, cooling the ears is a highly efficient way to cool the head.

U.S. Pat. No. 6,392,196 to Lin discloses a thermal earmuff that provides electric heating to the earmuff.

U.S. Pat. No. 5,908,583 to Bary discloses an exothermic chemically heated ear warmer. Bary, however, employs a packet of exothermic heat dispensing material that is received within a slot in the ear covering portions.

U.S. Pat. No. 2,933,086 to Gray, discloses fluid filled ear muffs. The ear muffs in Gray, however, are liquid filled to provide protection against aerotitis caused by a pressure differential on the ear drum.

U.S. Pat. No. 4,674,134 to Lundin discloses Earmuffs having a sealing ring that includes liquid and foam plastic layers. Lundin, however, employs the liquid in the sealing ring within a sealed chamber.

While these units may be suitable for the particular purpose employed, or for general use, they would not be as suitable for the purposes of the present invention as disclosed hereafter.

SUMMARY OF THE INVENTION

It is an object of the invention to provide a device that helps to cool the head by cooling the ears. Accordingly the present invention contacts each ears with a cooling device and thereby removes heat from the head to have a cooling effect thereon.

It is another object of the invention to maintain the cooling devices against the ears without significantly encumbering or inconveniencing the user. Accordingly, the cooling devices are held within a pair of earmuffs to hold the cooling devices upon the head in an unobtrusive manner.

It is yet another object of the invention to provide earmuffs that are user-fillable with a cool liquid so that they can be quickly refreshed. Accordingly, the earmuffs have an internal reservoir within the cooling devices that allow the user to introduce chilled water thereinto.

It is a further object of the invention to provide earmuffs that can cool the user for an extended period of time. Accordingly, the ear muffs can be configured with multiple reservoirs or with a continuous reservoir that extends through the connecting band and into each ear muff.

The invention is a pair of cooling ear muffs, for use by a user in cooling the head of the user. A pair of ear covers each have a shell and contain a reservoir for holding a chilled liquid. A sealing ring on each ear cover encircles the ear and a thermal membrane communicates heat from the ear to the reservoir. A connecting band extends between the ear covers for maintaining the ear muffs on the head of the user while holding the ear covers in position on the ears.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
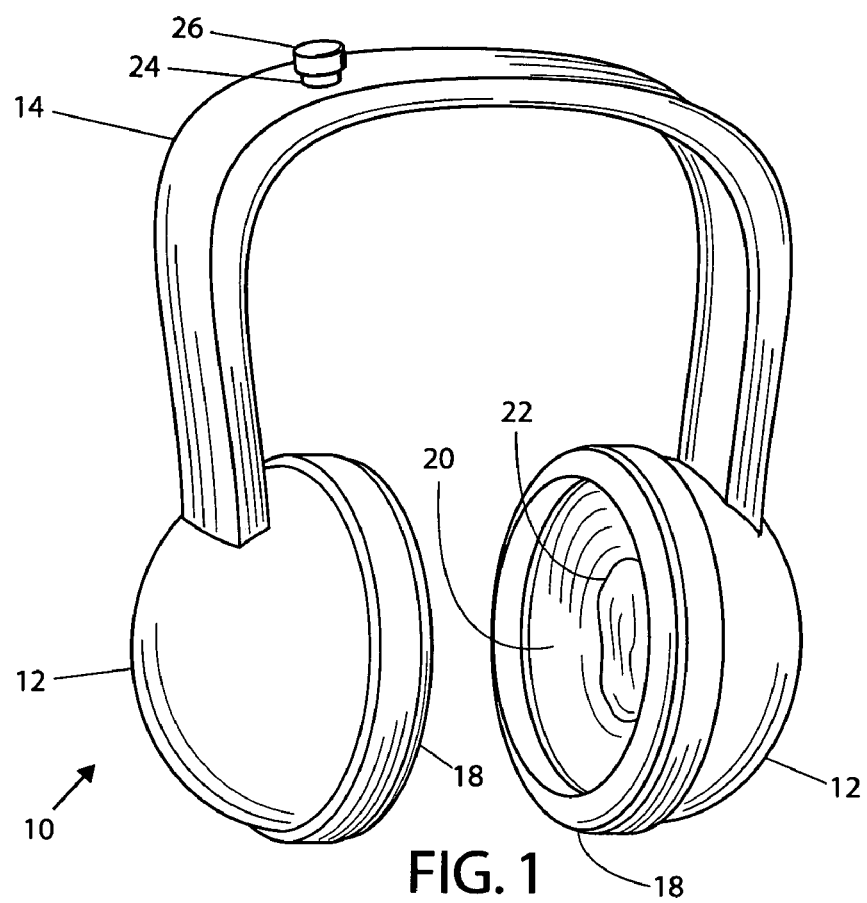
FIG. 1 is a diagrammatic perspective view, illustrating a pair of ear muffs, according to the present invention.
Figure 2:
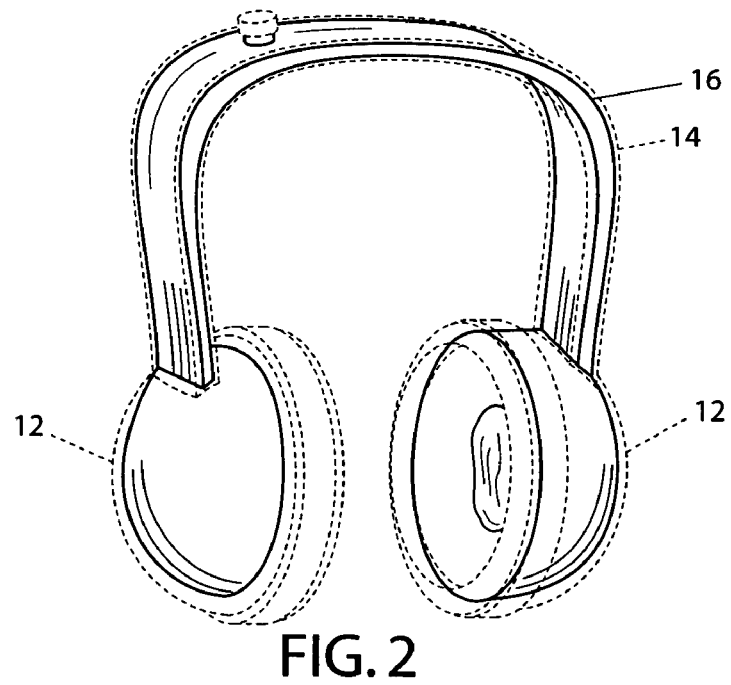
FIG. 2 is a diagrammatic perspective view thereof, illustrating the reservoir portion in full lines and external features in phantom.

FIG. 1 illustrates a pair of cooling ear muffs 10 according to the present invention for use by a user having a head and a pair of ears. The cooling ear muffs 10 have two individual ear covers 12, and a connecting band 14 for extending over the head of the user while engaging the ears with the ear covers 12. The connecting band 14 is securely attached to each of the ear covers 12. In the embodiment illustrated in FIG. 1 and FIG. 2, a reservoir 16 extends contiguous within both ear covers 12 and the connecting band 14, as indicated by FIG. 2.

Each ear cover 12 has a sealing ring 18 that encircles the ear, and a conical insert 20 that extends adjacent to the ear. A thermal membrane 22 extends concentrically within the conical insert 20 to directly contact the ear while the cooling ear muffs 10 are being worn. The reservoir 16 is in direct communication with the thermal membrane 22 so that chilled water within the reservoir 16 can effectively remove heat from the ear, through the thermal membrane 22, when the thermal membrane is in contact therewith. The reservoir extending through the connecting band 14 allows a significant quantity of chilled water to be stored, having a significant thermal mass, and thereby allowing a significant quantity of heat to be removed from the head before the chilled water warms to near ambient temperature. The connecting band 14 has a fill tube 24 that is in communication with the reservoir 16, and is selectively covered with a fill plug 26.

Figure 3:
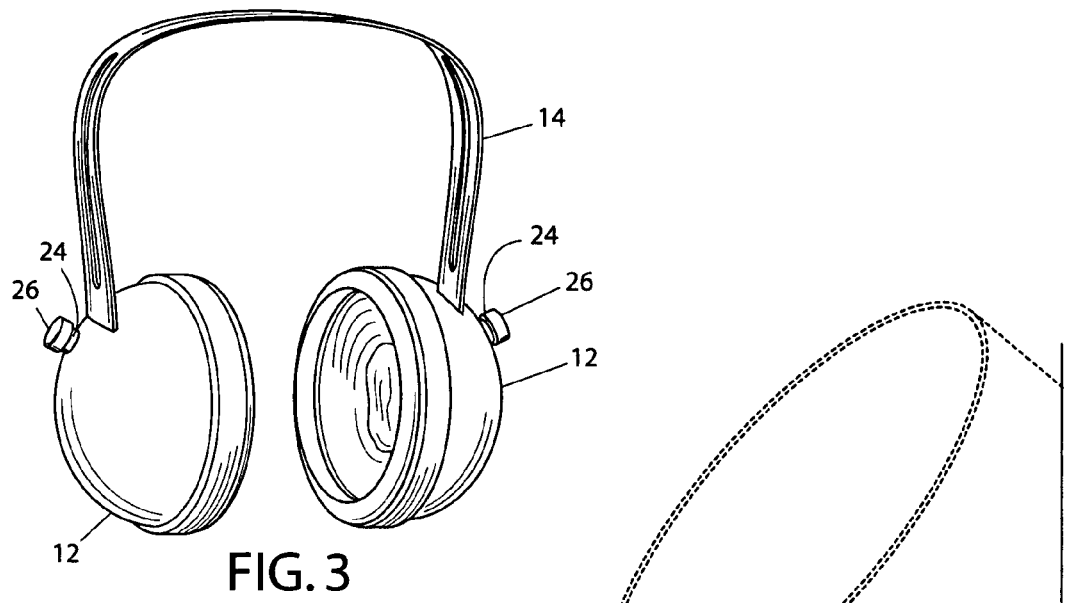
FIG. 3 is a diagrammatic perspective view, illustrating a further embodiment of the invention.

FIG. 3 illustrates a further embodiment of the invention, wherein each of the ear covers 12 are independently fillable, and wherein the connecting band 14 does not contain a reservoir, and there is no fluid communication between the ear covers 12. Accordingly, each of the ear covers 12 has a reservoir 16 that is accessible through the fill tube 24 that is selectively covered with a fill cap 26.

Figure 4:
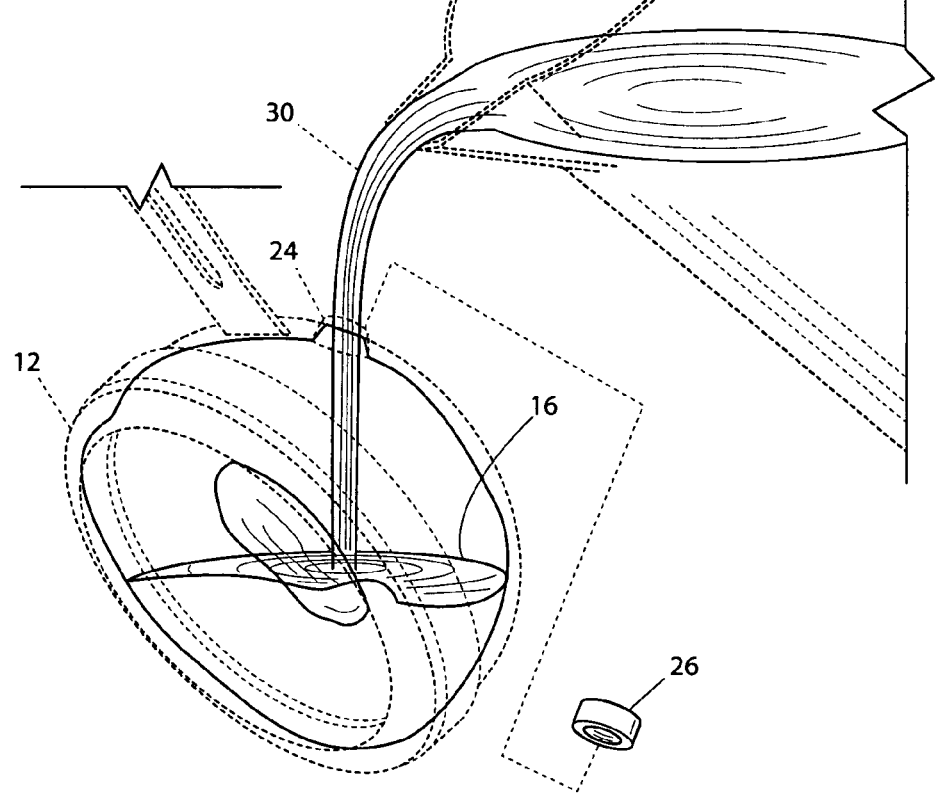
FIG. 4 is a diagrammatic perspective view, illustrating the internal reservoir thereof being filled by a user through a fill hole.

FIG. 4 shows a portion of the ear muffs 10, wherein the fill cap 26 has been removed from the fill tube 24 of one of the ear covers 12. The reservoir 16 is being filled with chilled water 30 by the user, by pouring said water 30 into the fill tube 24 of said ear cover 12.

Figure 5:
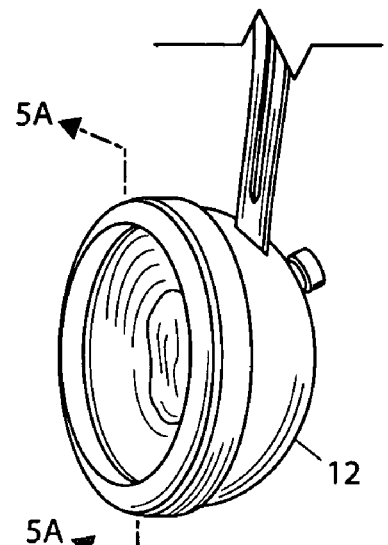
FIG. 5 is a diagrammatic perspective view, illustrating one of the ear muffs.
Figure 5A:
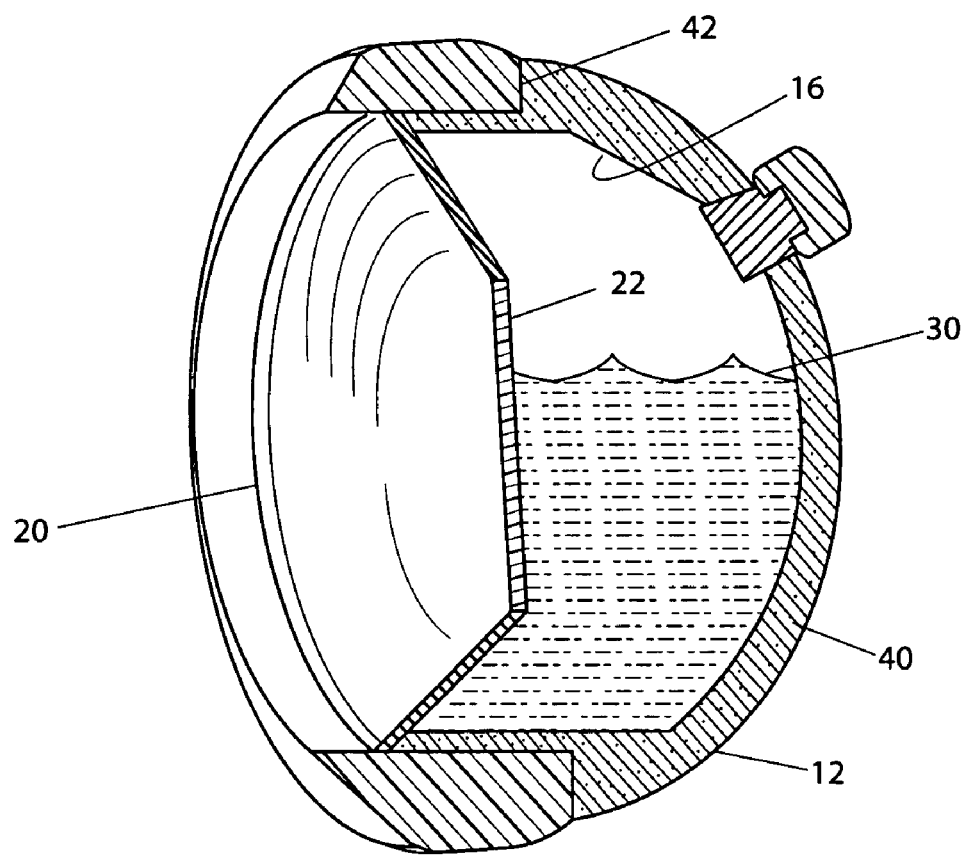
FIG. 5A is a cross sectional view, with parts broken away, illustrating the reservoir within one of the ear muffs.

FIG. 5 illustrates one of the ear covers 12, and FIG. 5A illustrates that ear cover 12 broken away, revealing structural details thereof. In particular, the ear cover 12 has a shell 40, a sealing ring 42, and the conical insert 20. The conical insert 20 and shell 40 together define the reservoir 16 for containing the chilled water 30. The sealing ring 42 is mounted on the shell 40, and is preferably made of foam rubber. The thermal membrane 22 extends within the conical insert 20 and forms a liquid impervious barrier with the reservoir 16. The thermal membrane 22 allows heat to transfer between the ear of the wearer and the reservoir 16.

In conclusion, herein is presented cooling ear muffs. The invention is illustrated by example in the drawing figures, and throughout the written description. It should be understood that numerous variations are possible, while adhering to the inventive concept. Such variations are contemplated as being a part of the present invention.

What is claimed is:

1. A pair of cooling ear muffs, for use by a user having a head and ears, comprising:
    a pair of ear covers, each ear cover having a shell, a reservoir within the shell for containing cooled liquid, a sealing ring for encircling one of the ears of the user, a conical insert inwardly of the sealing ring, and a thermal membrane concentrically located within the conical insert for communicating heat between one of the ears of the user and the reservoir; and
    a connecting band secured to both the ear covers, for extending over the head of the user while maintaining the ear covers on the ears.

2. The cooling ear muffs as recited in claim 1, further comprising a fill tube for communicating the liquid to the reservoir.

3. The cooling ear muffs as recited in claim 2, wherein the sealing rings are constructed of foam rubber.

4. A pair of cooling ear muffs, for use by a user having a head and ears, comprising:
    a pair of ear covers, each ear cover having a shell, a sealing ring for encircling one of the ears of the user, and a thermal membrane inwardly of the ear cover for contacting one of the ears;
    a connecting band extending between the ear covers; and
    a reservoir extending within the ear covers and connecting band, contiguous between both ear covers through the connecting band, the reservoir in communication with the thermal membranes in each of the ear covers.

5. The cooling ear muffs as recited in claim 4, further comprising a fill tube located on the connecting band for introducing cooled liquids into the reservoir.

6. The cooling ear muffs, as recited in claim 5, wherein each ear cover further has a conical insert inwardly of the sealing ring, wherein the thermal membrane is concentrically located within the conical insert.

7. The cooling ear muffs as recited in claim 6, wherein the sealing rings are constructed of foam rubber.

* * * * *